(12) United States Patent
Ozer Armon et al.

(10) Patent No.: US 10,245,108 B2
(45) Date of Patent: Apr. 2, 2019

(54) APPARATUS AND METHOD FOR PRODUCING VERY SMALL MICROCHANNELS IN TISSUE

(71) Applicant: LUMENIS LTD., Yokneam Ilit (IL)

(72) Inventors: Zipora Ozer Armon, Tel Aviv (IL); Eyal Benisty, Kfar Hachoresh (IL); Arie Kraisler, Petach Tiqwa (IL); Roy Ramati, Ramat Hasharon (IL)

(73) Assignee: LUMENIS LTD. (IL)

( * ) Notice: Subject to any disclaimer, the term of this patent is extended or adjusted under 35 U.S.C. 154(b) by 0 days.

(21) Appl. No.: 15/679,118

(22) Filed: Aug. 16, 2017

(65) Prior Publication Data

US 2018/0110565 A1 Apr. 26, 2018

Related U.S. Application Data

(63) Continuation of application No. 15/453,693, filed on Mar. 8, 2017, now abandoned, which is a
(Continued)

(51) Int. Cl.
*A61B 18/20* (2006.01)
*A61B 18/14* (2006.01)
(Continued)

(52) U.S. Cl.
CPC .............. *A61B 18/203* (2013.01); *G02B 9/34* (2013.01); *G02B 13/04* (2013.01); *G02B 26/105* (2013.01); *A61B 18/14* (2013.01); *A61B 2018/00005* (2013.01); *A61B 2018/0047* (2013.01); *A61B 2018/00452* (2013.01); *A61B 2018/00458* (2013.01); *A61B 2018/20351* (2017.05)

(58) Field of Classification Search
CPC .......... A61B 18/203; A61B 18/14; A61B 2018/00005; A61B 2018/00452; A61B 2018/00458; A61B 2018/0047; A61B 2018/2085
USPC ............................................. 606/9
See application file for complete search history.

(56) References Cited

U.S. PATENT DOCUMENTS 3,748,021 A * 7/1973 Tajima .................. G02B 13/00
359/749
3,799,655 A * 3/1974 Laikin .................... G02B 9/34
359/753
(Continued)

OTHER PUBLICATIONS

Lumenis/Premium Aesthetics, AcuPulse Fractional CO2 Laser, AcuScan 120, (Published on Oct. 2, 2012), [YouTube Video Online], Retrieved from the Internet: <URL:https://www.youtube.com/watch?v=eaZ81aCqPxo>.

*Primary Examiner* — Rex R Holmes
*Assistant Examiner* — Vynn Huh
(74) *Attorney, Agent, or Firm* — ISUS Intellectual Property PLLC

(57) ABSTRACT

A lens system includes: a plurality of aligned lenses; a first lens having negative refractive power; a second lens having negative refractive power; a third lens with positive refractive power; and, a fourth lens with positive refractive power; a light beam transmitted through the first, second, third and fourth lenses is first diverged by the first and second lenses, collimated by the third lens and focused by the fourth lens to form a small spot at the focal plane.

3 Claims, 14 Drawing Sheets

Related U.S. Application Data continuation-in-part of application No. 14/735,171, filed on Jun. 10, 2015, now abandoned.

(60) Provisional application No. 62/010,472, filed on Jun. 11, 2014, provisional application No. 62/010,013, filed on Jun. 10, 2014.

(51) Int. Cl.
*A61B 18/00* (2006.01)
*G02B 13/04* (2006.01)
*G02B 9/34* (2006.01)
*G02B 26/10* (2006.01)

(56) References Cited

U.S. PATENT DOCUMENTS

| | | | |
|---|---|---|---|
| 5,582,752 A | * | 12/1996 | Zair ................ A61B 18/20 |
| | | | 219/121.66 |
| D621,506 S | | 8/2010 | Khen |
| 2006/0167531 A1 | | 7/2006 | Gertner |
| 2008/0172047 A1 | * | 7/2008 | Altshuler ............ A61B 5/441 |
| | | | 606/9 |
| 2013/0144280 A1 | | 6/2013 | Eckhouse |
| 2015/0133899 A1 | * | 5/2015 | Anderegg .......... A61F 9/00823 |
| | | | 606/3 |

\* cited by examiner

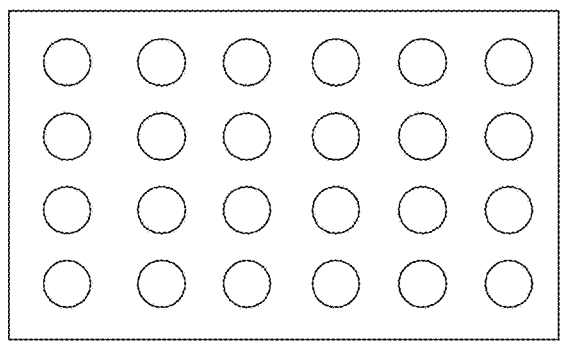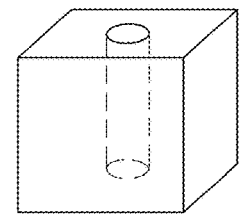
FIG.2A(1)
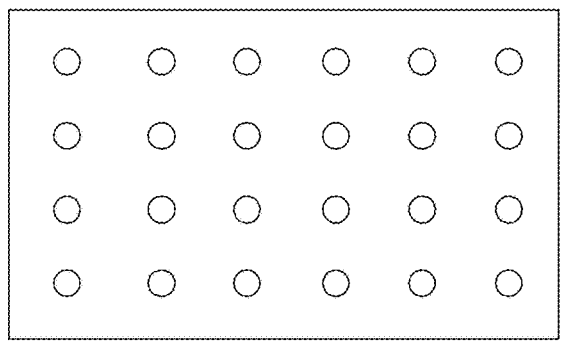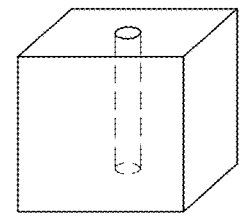
FIG.2A(2)
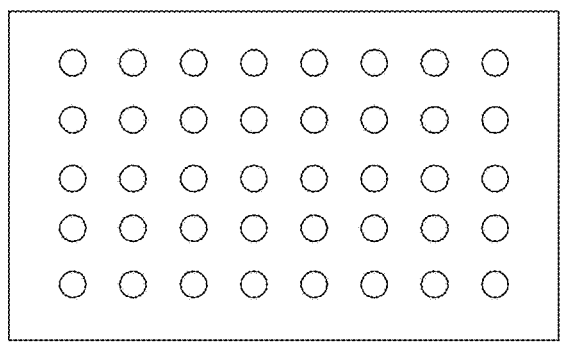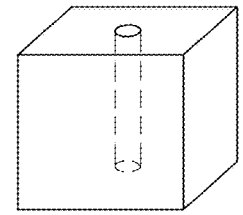
FIG.2A(3)

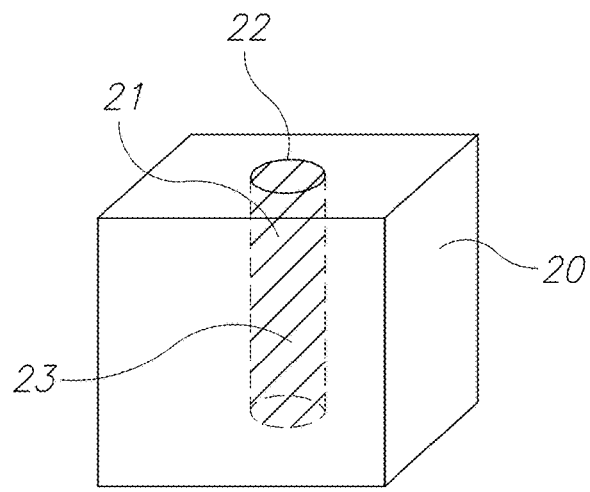
FIG.2B(1)
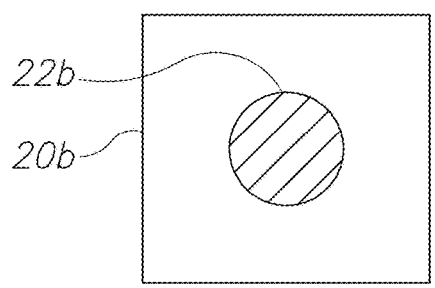 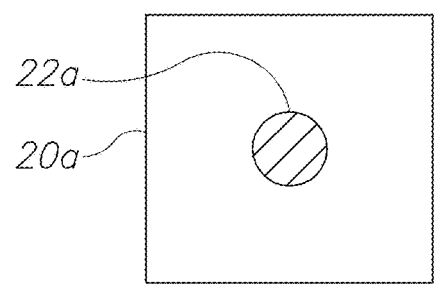
FIG.2B(2)   FIG.2B(3)

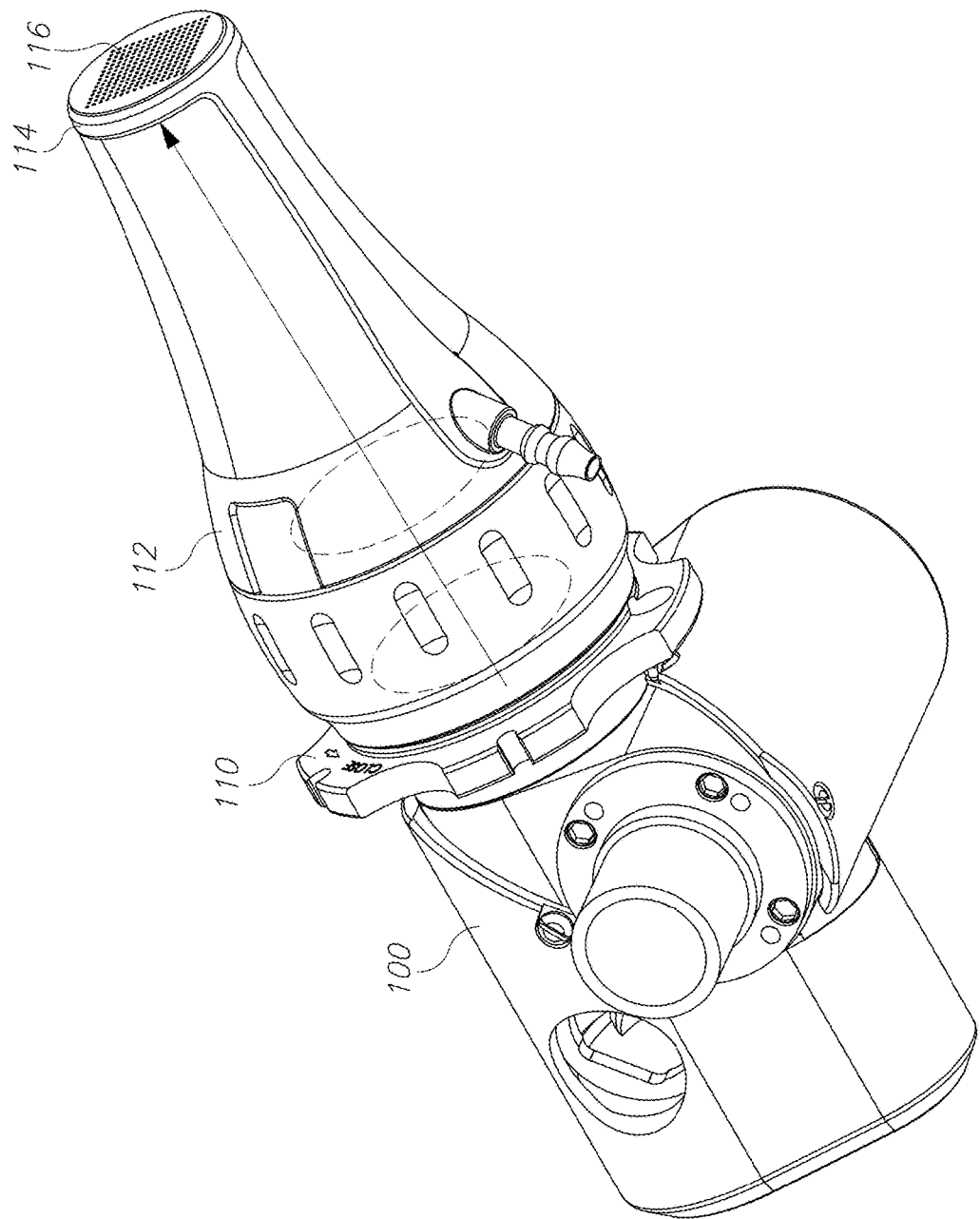

DIFFRACTION LIMITED SPOT-SIZE $$\text{SPOT SIZE DUE TO DIFFRACTION} = \frac{4M^2 \lambda f}{\pi D}$$

WHERE,
- $\lambda$   IS WAVELENGTH
- $f$   IS LENS FOCAL LENGTH
- $D$   IS INPUT BEAM DIAMETER AT THE LENS (AT THE 1/e POINT)
- $M^2$   IS THE BEAM MODE PARAMETER SPOT SIZE FORMULA ▨ FOR AcuPulse, $M^2 \sim 1.5$–$1.6$ ▨ FOR UltraPulse, $M^2 \sim 1.1$

| FOCAL DISTANCE | AcuPulse | UltraPulse |
|---|---|---|
| 54mm | 160 | 115 |
| 27mm | 80 | 57 |
| 10mm | 30 | 21 |

THEORETICAL SPOT SIZE [μm] DUE TO DIFFRACTION

FIG.9

APPARATUS AND METHOD FOR PRODUCING VERY SMALL MICROCHANNELS IN TISSUE

RELATED APPLICATIONS

This application is related to, claims priority to and is a continuation of U.S. application Ser. No. 14/453,693, filed Mar. 8, 2017, which is a continuation in part of U.S. application Ser. No. 14/735,171 filed Jun. 10, 2015, which application claims priority to U.S. Provisional Application Ser. No. 62/010,472, filed Jun. 11, 2014 and U.S. Provisional Application Ser. No. 62/010,013, filed Jun. 10, 2014, the entire disclosures of all of the above are hereby incorporated by reference. This invention is also related to U.S. patent application Ser. No. 13/314,548, and entitled: System and Method for Micro-ablation of tissue. More related inventions are U.S. Pat. Nos. 5,582,752; 5,798,498; 5,814,042; 5,618,285; 5,411,502; RE36872; 5,743,902; 5,957,915; 6,328,733. All of the above applications and patents are herein incorporated by reference in their entirety.

FIELD OF THE INVENTION

The present invention relates to the formation of microchannels in human tissue in a fractional treatment using a laser scanner or other laser device.

BACKGROUND OF THE PRESENT INVENTION

There exists an ongoing demand for procedures to improve skin defects. These defects may include wrinkles, old or loose skin, irregular pigment distribution, sun damaged skin and other defects formed on or in the skin tissue surface. Heretofore, such skin defects have been treated by two general approaches using energy based devices, 1) Full area skin resurfacing and 2) Fractional skin resurfacing.

Full area skin resurfacing treatments involved treating the entire surface of the effected skin. Both ablative and non-ablative energy sources were used, producing a full area injury that would promote healing and new collagens restoring the structures lost due to the skin defects. The ablative variety would use continuous scanning devices to remove the upper portion of the skin and the resultant healing response would, under the right conditions, produce a very good result. Such techniques were very aggressive, were painful to the patient, would have lengthening recovery times where patients had to avoid sun exposure, and had a potential for complications. The non-ablative full area skin resurfacing mode would heat the deeper dermal layers without heating the upper epidermis. By cooling the surface of the skin and focusing electromagnetic energy such as that from a laser device, a selected dermal damage region can be achieved while leaving the epidermis undamaged. This modality exhibited lower recovery times but lacked efficacy when compared to the ablative approach. At times, both ablative and not ablative treatments are combined to produce desired curative results to the skin tissue Fractional skin resurfacing was recently invented, in which a pulsed laser scans a tissue area to create a discrete pattern of ablative or non-ablative lesions leaving untreated areas of skin, theoretically treating only a fraction of the skin, which would heal faster than the previous full area resurfacing method. During this healing process, new skin is formed and new collagen forms, resulting in reversing the appearance of the skin defects. It is important to keep the volume of treated skin low to keep the healing response controlled and to avoid creating complications. Once a channel has been drilled into the skin surface, it is known to further treat the subsurface skin by performing a non-ablative treatment under which the interior surfaces of the channel as well as a bottom of the channel are heated to a degree to cause collagen remodeling. Such techniques are disclosed in U.S. application Ser. No. 13/314,548, an application assigned to the assignee of the present invention.

Of these two approaches, in terms of downtime and safety, due to limited exposure to complications, the fractional skin resurfacing approach is preferred, however, the efficacy of the full resurfacing approach is preferred. It is hypothesized that a ratio of optimized smaller spots, or shapes, can be created in an optimized fractional skin resurfacing modality to decrease the downtime, provide more comfort to the patient, and improve the efficacy over the devices of today. The challenge is the technological limitations of present day laser devices which do not permit the formation of very small narrow channels in a practical way. An optical configuration in a laser scanner may be created to be able to focus the treatment beam into a small focal point but the solution would involve more expensive optics, could require a short focal length complicating the scanner design by forming the optics to be too close to the targeted skin area and the scanner and raise the potential for debris contamination of the optics. What is needed is an apparatus and method for producing very small channels in tissue. It is to this goal that the present invention is directed.

SUMMARY OF THE PRESENT INVENTION

In an aspect, a lens system includes a plurality of aligned lenses, including a first lens having negative refractive power, a second lens having negative refractive power, a third lens with positive refractive power and, a fourth lens with positive refractive power. A light beam transmitted through the first, second, third and fourth lenses is first diverged by the first and second lenses, collimated by the third lens and focused by the fourth lens to form a small spot at the focal plane. The plurality of lenses act as a reverse telephoto lens system.

In another aspect, in the lens system, the back focal length (BFL) of the lens system is longer than the effective focal length (EFL).

In a further aspect, the spot size of the small spot produced is about 70 um at a distance of about 50 mm from the vertex of the fourth lens to the focal plane and the long BFL is about 50 mm.

In yet another aspect, the lens system may further include one or more scanning mirrors in line with and upstream of the plurality of aligned lenses and a source of laser energy upstream of the one or more scanning mirrors; the laser light beam from the laser source may be transmitted from the source of laser energy, deflected by the one or more scanning mirrors and then transmitted through the aligned lenses.

In yet a further aspect, the laser light beam is about 7 mm in diameter, diverges to about 12 mm after being transmitted through the first and the second lenses, enters the third lens with about a 12 mm diameter, and converges to 70 microns on the focal plane after being transmitted through the third and fourth lenses.

In an aspect, the radii of curvature of each of the first, second, third and fourth lenses may be selected to diverge and then converge a laser light beam to a spot size of 70 um.

In another aspect, the lens system may include one or more motors to control the one or more scanning mirrors, a programmed controller in operative connection to the one or more motors; the controller may be programmed to move the one or more scanning mirrors in a selected pattern.

In a further aspect, the first lens is of meniscus shape with radii of curvature of 20.61 mm and 50.15 mm, the second lens is of meniscus shape with radii of curvature of 35.1 mm and 28.35 mm, the third and fourth lenses are identical and of meniscus shape with radii of curvature of 163.35 mm and 61.19 mm.

In an aspect, a method of producing small microchannels on skin tissue includes: providing the above-described lens system; transmitting a light beam of about 7 mm in diameter to impinge on the first lens; transmitting the light beam through the first and second lenses, whereby the light beam diverges to about 12 mm; transmitting the diverged light beam to the third lens, the third lens collimating the light beam; and, transmitting the light beam from the third lens to the fourth lens, the fourth lens converging the light beam on the focal plane to 70 um.

In another aspect, an apparatus for producing microchannels in the skin tissue includes a handpiece; the handpiece is connected to a source of light energy and has opening therein, a proximal portion through which the light energy is received and a distal portion through which the light energy leaves the handpiece, It further includes an apertured plate having a plurality of apertures formed therein mounted on the handpiece; the apertured plate blocks light energy from leaving the handpiece except through the apertures in the apertured plate.

In another aspect, the apertured plate is mounted in the vicinity of the distal portion of the handpiece.

In yet another aspect, the light energy source is laser light energy and is delivered in the form of a laser scanning device.

In a further aspect, the distal portion of the handpiece in is the shape of a cone, the cone decreasing in size for its proximal end to its distal end and the apertured plate is mounted on the distal end of the cone. The apertures range in size from 50 um to 100 um and the distance between the apertures ranges from 50 um to 200 um.

BRIEF DESCRIPTION OF THE DRAWING FIGURES

FIG. 1 illustrates a prior art device for producing microchannels.

FIGS. 2A (1) to (3) and 2B (1) to (3) illustrate various type of channels formed in the skin tissue.

FIGS. 4A and 4B illustrate different views of the device of FIG. 3.

FIGS. 6, 7A and 7B, and 8A to 8C illustrate the results of tests of a laser device equipped with and without an apertured plate.

FIG. 9 illustrates theoretical minimal spot sizes producible by a laser device.

Figure 4B:
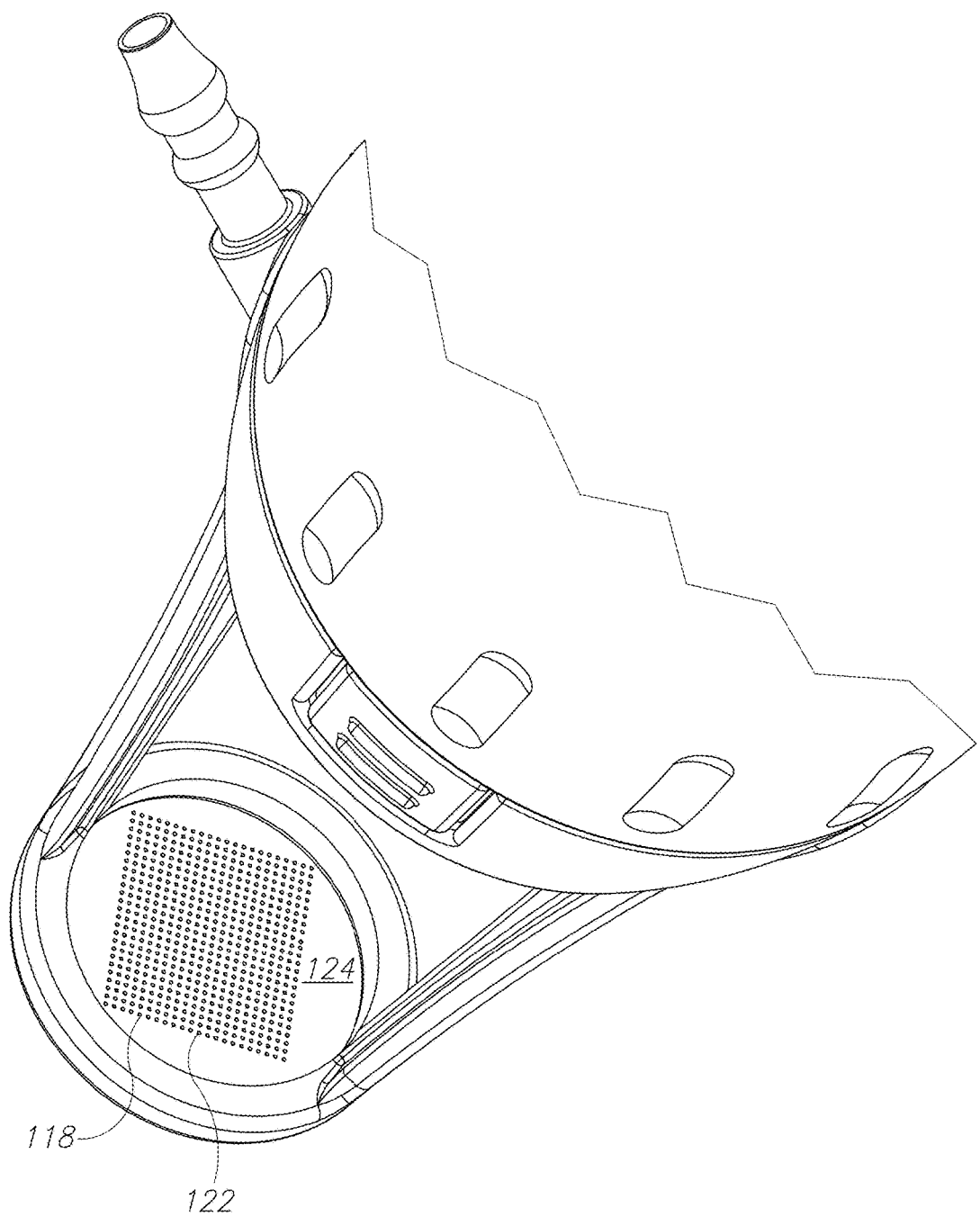
Figure 10:
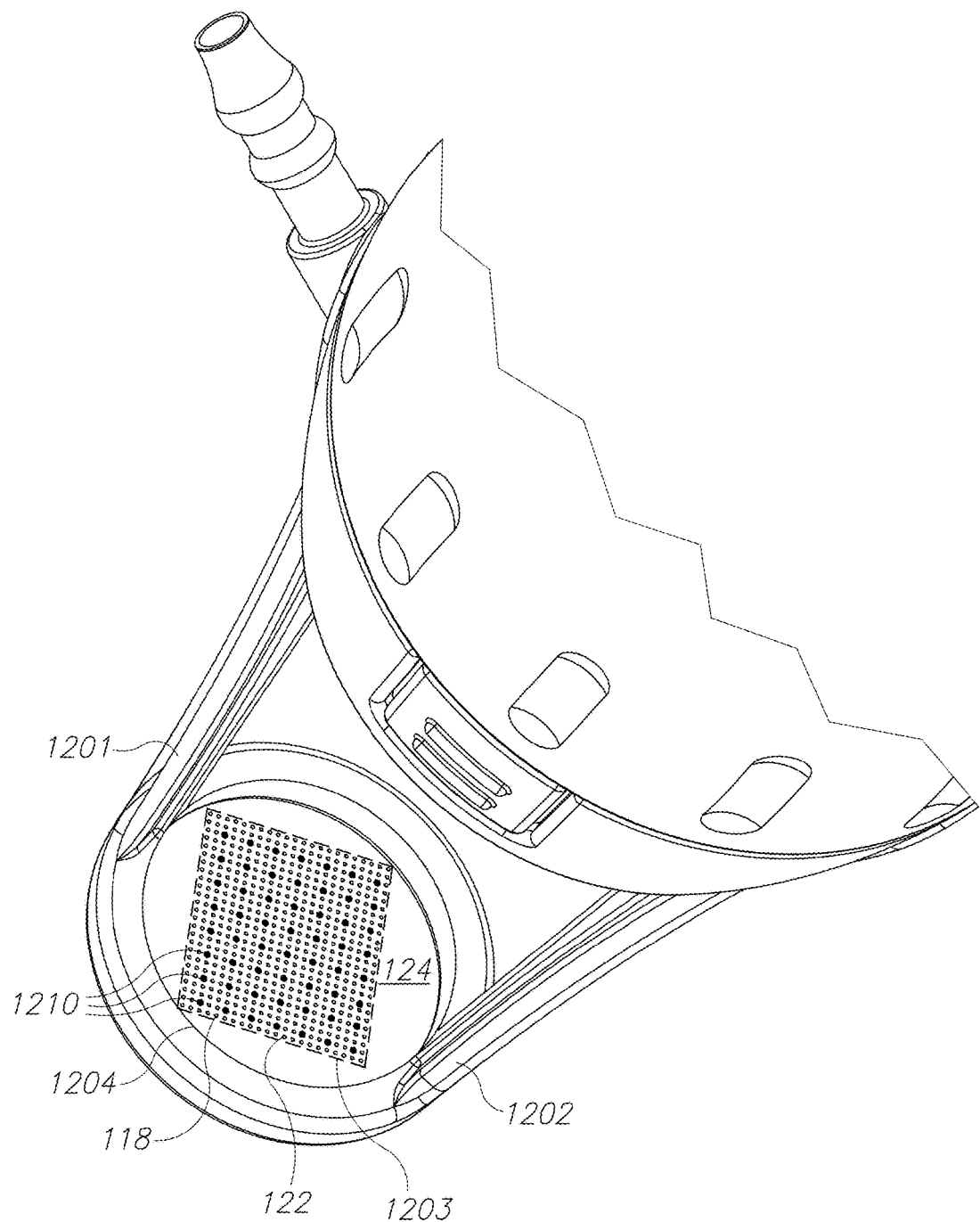

FIG. 10 illustrates a modification of the device of FIGS. 4A to 4B.

Figure 11:
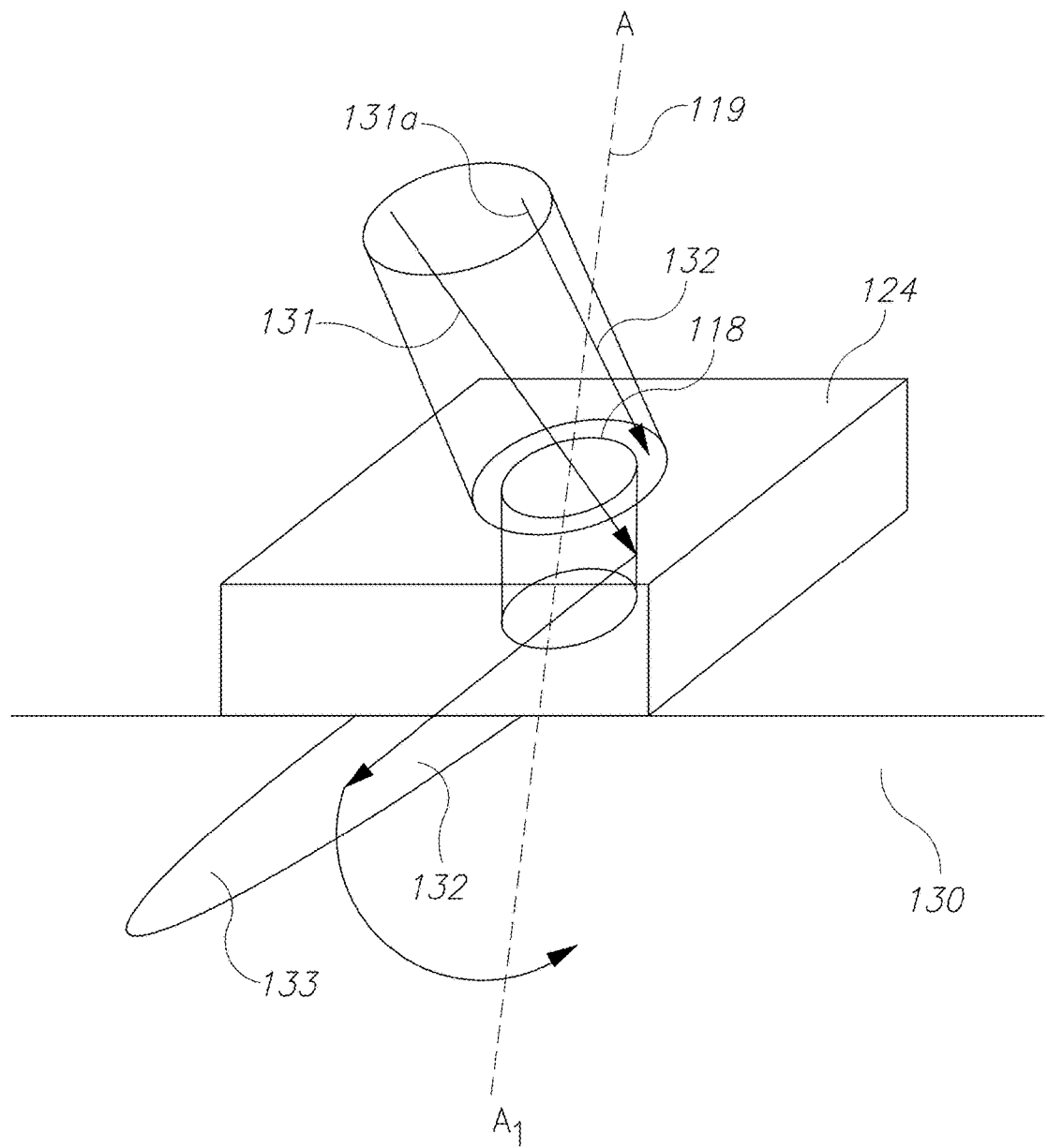

FIG. 11 illustrates a beam of laser energy entering an aperture in the apertured plate entering the aperture at an angle.

Figure 12A:
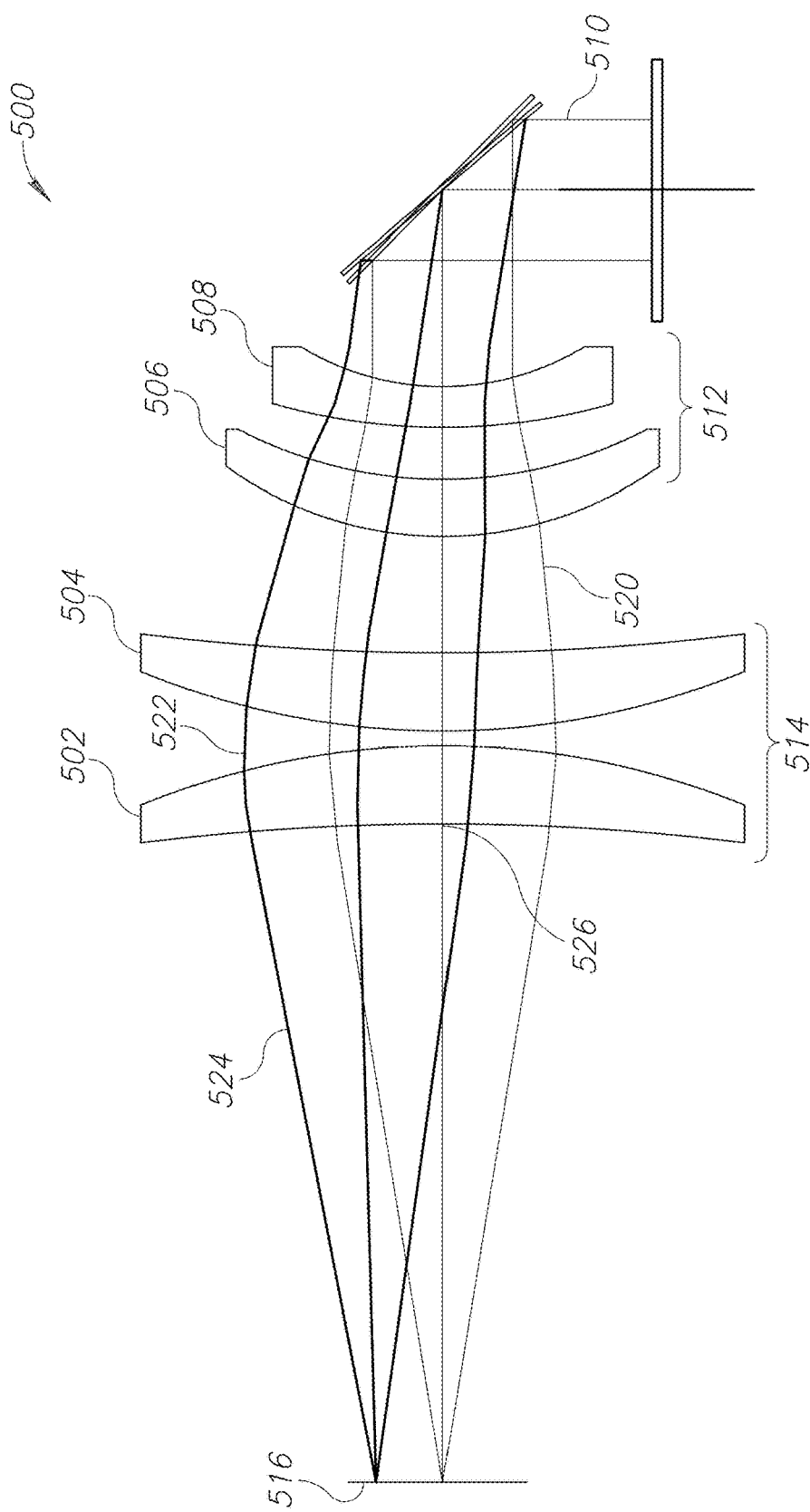
Figure 12B:
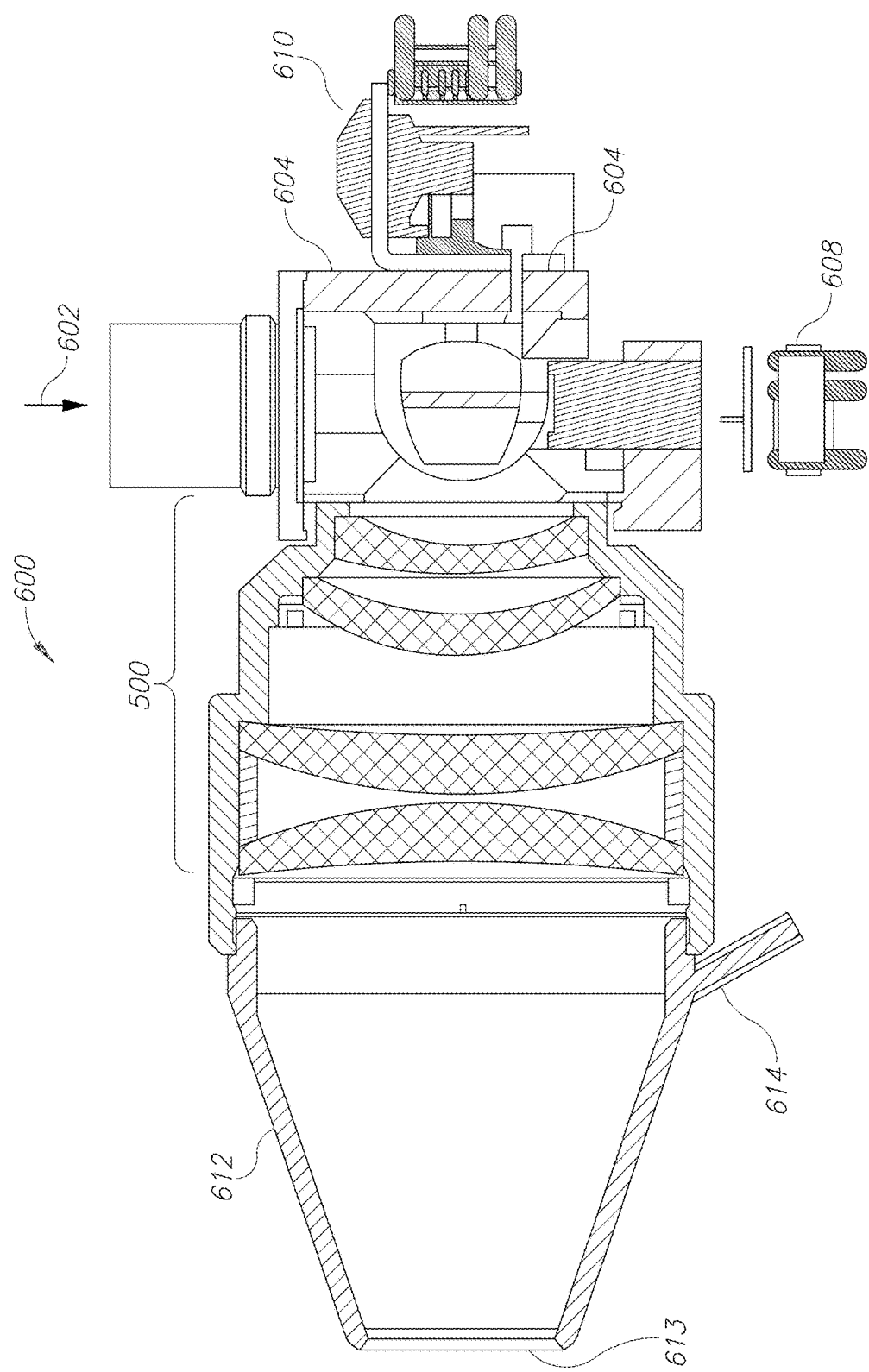

FIGS. 12A and 12B illustrate an optical system for providing small microchannels in the skin tissue.

DETAILED DESCRIPTION OF THE PRESENT INVENTION

Figure 1:
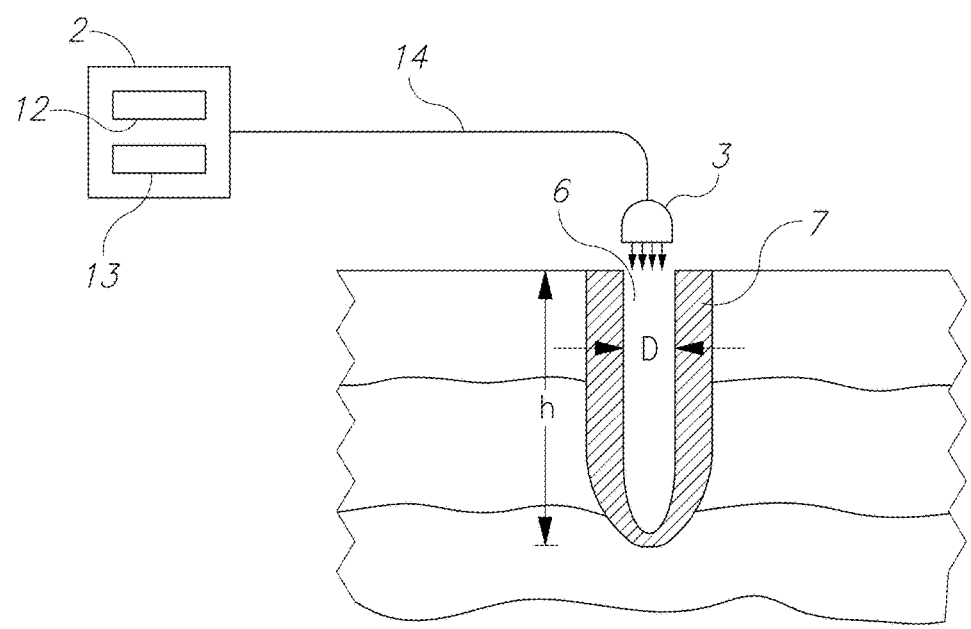

One prior art device, assigned to the assignee of the present invention, is illustrated in FIG. 1. That prior art invention may be found described in U.S. Ser. Nos. 12/799,064 and 12/928,228, the entire disclosures of which are herein incorporated by reference. The reference numerals correspond to the reference numerals in Ser. No. 12/928,228. The present invention is directed to an apparatus for producing very small channels in human skin tissue. The benefits of very small channels being formed in the course of a fractional treatment are that healing is improved in terms of time and in terms of discomfort or pain to the patient. Also, it has been found that using many very small channels provides better results on skin tissue than with fewer, larger sizes channels.

Turning now to FIGS. 2A and 2B, these figures illustrate the various type of channels that may be formed in human tissue. As can be seen in FIG. 2A(1), this figure shows a number of deep yet wide channels that are formed in the skin tissue. Due to the diameter of these spots, only a certain number of spots can be placed into a given tissue surface area to prevent complications. In FIG. 2A (2), it is seen that the diameter of the spots has been reduced. However, as seen in FIG. 2A (3), due to the diameter of the small spots a larger number of channels can be accommodated in the same area of skin tissue as shown in FIG. 2A (1).

Turning now to FIG. 2B, this figure illustrates the concepts behind the present invention of providing many very small channels. First, it is to be understood that healing time is determined by the surface area of the spot/channel made on the skin surface. The smaller the spot, the faster the skin can grow in toward the center to close the lesion. The bigger the spot the longer to close and thus more downtime. As seen in FIG. 2B (1), a micro channel 21 located in a skin volume 20 has an upper two-dimensional surface 22 located on the skin surface and an inner three-dimensional surface 23 located in a skin volume. A top view on different skin volumes 20a and 20b (FIGS. 2B (2) and (3)) shows respectively upper two dimensional surfaces 22a and 22b of two micro channels having different diameters. The smaller the accumulated and ablated surfaces 22 on the skin the faster the healing time and the lower the chances for contamination and complications.

Therefore, according to one aspect of the invention there is a need to reduce the size of ablated areas 22. However, the larger the area of the volume surface 23 in the skin the better efficacy and clinical outcome of the treatment. Therefore, according to another aspect of the invention there is a need to increase the three-dimensional volumes 23 in the skin. A smaller skin surface area 22 will likely result in a shorter downtime or time to heal. Increasing the number of small spots so the overall treated area of the skin is the same as the larger spots will result in an overall equal treated volume assuming equivalent depth, yet making them smaller results in larger volume surface area 23 of the channels which in turn leads to better efficiency and shorter downtime as well as less discomfort and pain to the patient.

In the present invention, two separate but related improvements to the present technologies may result in the ability of providing a large number of very small channels in a given area of skin tissue.

A first embodiment works by providing improvements to present day fractional resurfacing technologies by modifying the optics of a laser scanner device itself. A laser scanner device which is available from the assignee of the present invention, Lumenis Ltd., is named the "AcuScan". This device, illustrated in FIG. 3, includes a source of the laser power namely, a CO2 laser device. The laser beam emanating from the CO2 laser is directed to a series of servo-controlled mirrors which are under the control of a computer system. In a known technique, the mirrors are directed to output a series of narrow beams of laser energy which are sent to the skin tissue in a selected pattern. The size of the beam spot, the number of spots per unit area, the amount of energy imparted to the skin tissue at each beam spot, and the shape of the pattern formed upon the skin tissue are all selectable, within the capacity of the system, under the computer controller of the apparatus. The assignee of the present invention is also the assignee of a number of patents covering the above-described apparatus. These patents include: U.S. Pat. Nos. 5,743,902; 5,957,915; 6,328,733; 5,582,752; 5,798,498, 5,814,042; 5,411,502; 5,618,285

Figure 3:
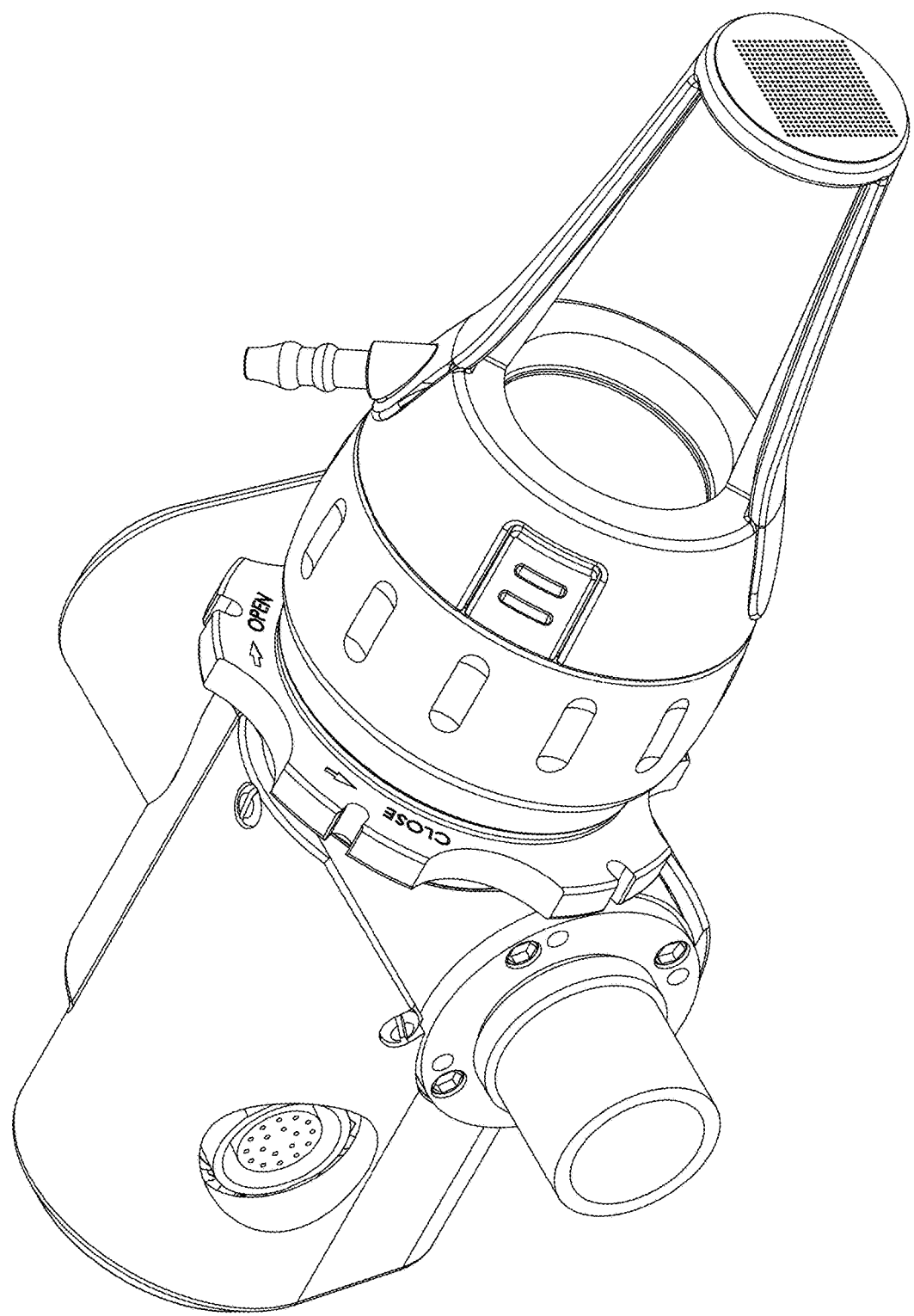
FIG. 3 illustrates a known laser device with scanning capabilities with an apertured plate mounted in the distal end of a head.

At present, the apparatus shown in FIG. 3 has the ability to produce discrete patterns of microchannels by scanning a pulsed laser beam in a pattern, such a laser beam having spot sizes on tissue surface which may range, for example, from about 80μ to about 1300μ. For example, a CO2 laser may use a spot size ranging from about 120μ to about 160μ for ablative treatments at a focal distance of 54 mm. In order to produce narrower channels at the same working distance, the apparatus of FIG. 3 may be modified.

Several options may be combined. First, the beam diameter before the lens may be increased in size to allow for better focusing of the beam, thus allowing for a narrower spot size and therefore smaller channel diameter. Another technique is to replace the optics and decrease its focal length (the distance from the lens of the scanner to the minimum spot size of the beam). This, again, may allow for a narrower beam. However, by moving the scanner closer to the skin surface (the working distance is the focal distance to achieve enhanced ablation), one potential disadvantage is that the operator may not be able to see the effects of the laser beam on the skin tissue due to the obstruction of the scanner being too close to the skin surface. A further potential disadvantage is that when channels are being formed by ablating "vaporizing" tissue, ablated tissue debris from the ablation floats around the skin surface area and may cause the optics in the apparatus to become dirty and thus lower the efficiency of the optics through which the channels are being formed.

Another potential disadvantage is that the scan pattern will be smaller for a given beam size at the input of the scanner or on the skin (Note that for a reverse telephoto arrangement the BFL has been increased but the EFL (focal length) remains short). Another potential disadvantage is that the shorter the focal distance the more susceptible the spot size and shape when the beam is not fully perpendicular to the skin. In a scan pattern, the beam has been found to be more perpendicular to the skin in the central scanning zone and less perpendicular in the periphery of the scanning zone. As a result, the spot smears, loses its focus and becomes more oval in shape. Ablation efficiency may be decreased and the holes' size increased. A technique to overcome the last disadvantage may be to (design a telecentric scanning lens whereby the scanned beam is always perpendicular to the tissue) increase the diameter of the input beam and the size of the focusing lens, but there may not be sufficient room within the scanner mechanism to allow this to be easily accomplished.

In another technique, a wholly redesigned optical system has been developed to allow for smaller microchannel diameters while at the same time allowing the end of the device to stand off the skin tissue surface a sufficient distance so that the operator may observe what he/she is doing and to lessen the amount of skin debris which can cause dirtying of the system optics. Furthermore, the redesigned optical system is near telecentric.

Turning now to FIGS. 12A and 12B, these related figures illustrate the overall structure and arrangement of the new lens system of the present invention. The lens system 500 includes, in this embodiment, 4 lens elements 502, 504, 506 and 508 which together comprise the scanner lens system which has the following properties.

The 4 lens elements together create a scanning lens.

An input parallel beam 510 from the scanner mirrors (not shown) is focused such that the minimum spot diameter lies at the focal plane of the lens.

All the scanned spots are near telecentric. Telecentricity ensures that the chief rays of the spots are parallel to the optical axis of the lens.

This is a desirable effect because this arrangement maintains the scan pattern (magnification) at different depths of the tissue and therefore constitutes that the center beam of each scanned spot is perpendicular to the tissue The lens system 500 acts not only as a not only a scanning lens but also as a reverse telephoto lens. What this means is that the back focal length (BFL) is longer than the effective focal length (EFL). The BFL of a lens or lens system is the distance from the final optical element within a system to the back (rear) image point of the system. The EFL of a lens system is the distance from the principal point to the focal point.

This feature is necessary when working distances above a certain minimum are required while maintaining sufficiently small spot sizes.

A telephoto lens arrangement (or reverse telephoto in this instance) serves to expand the parallel collimated input beam 510 before focusing it down to the focal plane, if the lens system 500 is split into two sections 512 and 514, the first section 512 serves as a beam expander which expands the input laser beam, as can be seen in the figure. The second part 514 of the lens system 500 then focuses this beam at the working plane 516. As mentioned, smaller spot sizes than are conventionally known are desirable to increase the power density for the treatment.

Long BFLs are desirable to facilitate operation of the device where a very short BFL (discussed above) would inhibit the surgeon's hands, tools, etc. during the procedure. Thus, a small spot size=a small EFL and a long working distance=a large BFL)

Whereas the combination of the 4 elements 502, 504, 506 and 508 comprise the scan lens, the individual elements may be described as each having a certain purpose. In the system illustrated in FIG. 12A, mono-chromatic aberrations are corrected. These same aberrations are spherical aberration, coma, astigmatism and distortion. The present arrangement and the combination of all the 4 elements together correct for all these aberrations while maintaining the constraints of BFL larger than EFL (reverse telephoto) and telecentricity.

One way of describing the system is as follows:—

Lens 508 (closest to the scanner mirrors) may be constructed from a ZnSe material and is a negative lens which expands the laser beam by creating a diverging beam (as shown).

Refraction of the beam through lens 506, which is a positive lens, also constructed from ZnSe, reduces the amount of divergence created by the first lens 508. A positive lens is a lens which converges light and a negative lens is one which diverges or spreads light.

Lens 504, which may be constructed from ZnSe tends to collimate the beam expanded beam.

Lens 502 (which is identical in shape to lens 504), which also may be constructed from ZnSe, focuses the collimated beam at the working plane 516.

The chief ray of the collimated beam (the chief ray is the central ray) after refraction through lens 504 apparently crosses the optical axis of the lenses at a distance equivalent to the focal length of lens 502.

If this condition is met then the focused beam at the working plane is telecentric.

Turning now to FIG. 12B, this figure illustrates the placement of the lens system 50 within an apparatus 600. An input beam 602, likely a laser beam, enters into a housing 604 which contains (as is conventionally known) a Y-axis scanning mirror (not shown) driven and controlled by a Y motor 608 as well as an X-axis mirror (not shown) driven by a X motor 610. The scanning mirrors act together, as in the prior art patent mentioned above, to direct the laser beam 606 through the lens system 500 to impact on a substrate (human skin tissue) at various designated spots in a X-Y matrix on the skin tissue. A tip 612 is attached to the distal end of the device 600 and has an opening 613 through which the directed laser beam leaves the device 600 and impacts the skin tissue at desired spots. A gas fitting 614 may be connected to a source of positive air pressure to cause any debris form the laser operation to be deflected away from the lens system 500.

While appearing counter-intuitive, in order to achieve a small spot size on the target skin tissue, the size of the light beam coming into the lens system should be large. This is because the larger the size of the beam on the focusing lens, the smaller spot size a lens can produce. For example, if d is the spot size on the skin tissue, and D is the spot size on the focusing lens, then d is proportional to 1/D.

Presently, in the devices of the assignor discussed above, the typical input beam is 7 mm in diameter. Remember that the desire is to produce a 70 micron spot size on the skin tissue. The 7 mm beam is not sufficiently large to produce a 70-micron spot size. Thus, lenses 506 and 508 serve to diverge the incoming beam 500 (FIG. 12A). The second lens 506 corrects for optical aberrations caused by the first lens 508. The first lens 508 is not necessarily uniform in thickness, as may be seen in the figure. Instead, the lens 508 is seen to be thinner in the center than going out from the center. The second lens 506 may be constructed in just the opposite fashion, that is, the center of the lens is thicker and gets thinner going away from the center.

The art and object of optical design is to carefully correct for aberrations by "shaping" the lenses. It Is not really to the shape of the lens or lenses, whether they be plano-convex or plano-concave, bi-convex or bi-concave or a meniscus (which is concave-concave or convex-convex). Refraction at each of the 8 surfaces (4 lenses with each a "front" and a "back" surface totaling 8) produces aberrations. The surfaces need together to counteract these aberrations. So, for example, while refraction through surfaces 1 to 4 might create strong positive spherical aberration, then the lenses are shaped so that refraction through surfaces 5 to 8 will produce the same amount of negative spherical aberration thereby counteracting the positive spherical aberration from the first 4 surfaces. In such a way, the system will ultimately be aberration free or what is known as diffraction limited i.e. the spot size is defined by diffraction only and the lens itself does not contribute to (enlarge) the spot.

Thus, the light beams coming out of the lenses 506 and 508 at 520 are seen to have diverged from the input beam 510. Now, the design is to convert the diverging beam 520 into a parallel beam and this is what the lens 504 accomplishes, as seen at 522. Since the ultimate design is to produce small spot sizes on the skin tissue 516, the parallel beam 522 must now be converged and this is the function of lens 502 which is seen to provide a converging light beam 524 onto spots on skin tissue 516. As mentioned, the typical beam is about 7 mm in diameter. With the combination of the operation of lenses 508 and 506, the beam has been shown to be about 15 mm in diameter as it impinges on lens 504. With the present design, is has been shown that 70 micron microchannel spots may be formed on the skin tissue, with an approximately 50 mm distance between the skin tissue and the end portion 526 of the lens 502. This distance has been found to be sufficient to allow the operator a good view of the operation being performed as well as a sufficient distance to minimize debris impinging on the lens system.

Another embodiment that may be implemented, as illustrated in the embodiments shown in FIGS. 3, 4A and 4B. In this embodiment, the present day continuous scanner is not modified but rather between the scanner and the tissue surface a masking screen or mesh may be interposed. Turning now to FIG. 4A, this figure shows a scanner device 100 of the known type described above. Attached to the distal end 110 of the scanner is a head 112. Head 112 may be of a similar design to the interfacing head illustrated in U.S. Pat. No. D621,506 issued Aug. 10, 2010, and assigned to the assignee of the present invention. The entirety of the disclosure of the foregoing patent is herein incorporated by reference. In the head shown in FIG. 4A, the distal end 114 of the head contains a plate or surface which includes a number of very small holes 118 (see FIG. 4B). These small apertures or holes may have a diameter that ranges from 10 to 300 microns, while the distance between adjacent holes may range from 50 microns to 500 microns or be for example 200 microns or alternatively 150 microns or in another embodiment 50-100 microns or less. The spacing of apertures from one another in the apertured plate, and thus the apertures' "density", may be in accordance with the size of the apertured plate the size of the apertures themselves and may generally range from 100 um to 200 um distance between adjacent apertures. They may be arranged in a "square" fashion as shown in FIG. 4B, or may be in any selected pattern as desired and depending on the area of the skin tissue surface to be treated. Plate 116 may have a pattern of uniform holes distribution or a pattern with non-uniform holes distribution. Plate 116 may also have a pattern with a uniform hole size or a pattern having a non-uniform mix of hole sizes. Plate 116 may also have a pattern with holes that are not round, but take different forms. For example, holes having a star or a Star of David cross section may increase the inner surfaces 23 and decrease surfaces 22, as defined in FIG. 2B. As mentioned above, the higher the ratio of surface 23 over surface 22 the shorter healing time and better healing response. Therefore, according to another aspect of the present invention, there is a need to increase the ratio of surface 23 over surface 22 as defined in FIG. 2B. For example, a long rectangular shaped pattern of holes or apertures may be provided if, for example, the tissue surface to be treated is under the patient's eyes or above the upper lip. The technique for forming the apertures or holes may include laser drilling or metallization buildup as known in the process of making metal screens for screen printing. The plate itself may be of metal or any other suitable material or coating that can withstand being impinged upon by the treatment laser beam energy.

In addition, the head 112 may be comprised of an opaque and/or light reflective material, but in any case of a material which will not pass light, and in particular scattered laser light, out of the head. The reason for such scattering is that a series of laser light beams will travel generally along longitudinal axis 120 from the scanner optics towards the apertured plate 116 as seen in FIG. 4A. The scanner may operate in its "normal" mode, in which laser beams will be directed continuously across the surface of the apertured plate 116 by way of the servo motors and mirrors. During this scanning operation, some of the laser beams will pass directly through the apertures in the apertured plate 116 and will then impinge on the tissue surface, to be explained below. Other laser beams will not pass through the apertures but will hit either between the apertures or hit entirely outside the apertures as illustrated in surface 124. In that event, the light beam will, depending on the material on the "backside" of the apertured plate, be either absorbed or reflected or partially both.

If reflected, such laser beams may be scattered from the backside of the apertured plate and reflected in a number of directions but generally toward the scanner 110. The head may be constructed to possess an interior surface that is not only opaque to light (so such laser beams do not escape the head) but also of an absorptive material to absorb the laser beams. In the end, the diameter of the apertures in the plate will dictate the diameter of the channels formed into the skin surface.

While the scanner may be of the type disclosed above in connection with the '724 U.S. Pat. No. 5,618,285; USRE36872; U.S. Pat. Nos. 5,411,502; 5,582,752; 5,798,498; 5,814,042 family of patents, it may also be of the type shown in the '454 CPG family U.S. Pat. Nos. 5,743,902; 5,957,915; 6,328,722 of patents assigned to the assignee of the present invention. It may not be necessary to have the precision of the CPG apparatus to select and direct narrow beams at precise spot areas because in the present invention the plate itself acts as a "filter", permitting only beams to emerge from the plate through the holes or apertures and make precisely sized channels on skin tissue surface.

According to one aspect of the present invention, whether the scanner is a continuous scanning scanner or a pattern scanning scanner, the beam exiting the scanner and hitting the apertured plate may have a spot size which is bigger than the size of the holes in apertured plate 116. According to this embodiment, the footprint of the scanning laser may capture few holes in plate 116 and ablating multiple channels in the underlying skin simultaneously. If a pattern scanner is used the scanner may be programmed to cover the entire apertured plate 116 with minimum overlaps. However according to another embodiment any degree of overlap may also be required if more optical energy is needed to ablate deeper holes or to treat the bottom of the holes with a non-ablative laser. In addition, the sequence of scanning steps required to create a chosen pattern may differ due to various considerations among them is thermal relaxation time of the ablated tissue. Therefore, the sequence may be chosen to be random or to maximize the ability of the tissue to cool itself between successive laser shots by hitting spots in a sequence based on a fixed (look up table) or a dynamic algorithm which defines the biggest distance possible between two successive shots. Alternatively, if a continuous laser is used which has a spot size which captures multiple holes in aperture plate 116, depending on the scanning direction and speed spots under the scanned beam will experience light rising time, light time and light set time. Scanned beam, spot size and scanning speed and direction of the beam may be a function of the overall optical energy is needed per hole.

Thus, there may be a number of criteria and issues in the implementation of the aperture plate embodiment. These include: (a) selecting the right material both for the apertured plate as well as the head; (b) whether the aperture plate and/or the head are disposables or are not disposable but reusable; (c) the accuracy of shooting beams through the apertures in the aperture plate (for example, what percentage of beams pass through the apertures and what percentage are reflected away); and (d) how to deal with inevitable heating issues in the head and the plate itself.

It is to be expected that those laser beams that do not pass through the apertures will, to some extent, cause heating of the plate. The plate may, in operation, be placed directly on the skin surface during lasing, and this may cause the heat to be transferred to the patient's skin tissue. Cooling the head itself may lessen some of the heat transfer issue and cooling the apertured plate itself may also be implemented, particularly if the apertured plate is made of a metal that may be readily cooled. Use of a cooled apertured plate may also be beneficial in patient comfort and pain reduction. In addition, cooling the apertured plate may help cooling the untreated skin below the plate and around the micro channels. Cooling the tissue surrounding the micro channels may help keeping such micro channels open for a longer period of time. Keeping the patency of the micro channels is important when the micro channels have to deliver in or out of the skin one or more energy or substances FIG. 10 shows another aspect of the present invention. According to this other embodiment of the present invention, apertured plate 124 may consist of an at least one bulk electrode such as 1201, 1202, 1203, 1204, 1205, 1206, 1207 or 1208 or an array of electrodes such as 1201 configured to deliver RF treatment to at least a portion of the tissue underlying apertured plate 124. An RF driving module may be integrated into the laser system or be as an external module. Disposable head 112 may have electrical conductors 1220 and wires configured to be connected to RF driver and controller. According to one embodiment of the present invention, at least two opposing bi-polar electrodes may be positioned on opposing edges of the apertured plate. According to this embodiment, an RF energy may heat a bulk of tissue underlying the apertured plate. Such heating can be done before, during or after the application of the laser energy. A cooling system as mentioned above can be still applied to the apertured plate and/or the electrodes to cool the upper layers of the tissue. According to another aspect of the invention, an array of fractional electrodes may be positioned on the apertured plate configured to deliver an RF fractional treatment to the underlying tissue before, during or after the laser treatment. According to another embodiment of the present invention a combination of two or more bulk electrodes and an array of fractional electrodes may be practiced. In an embodiment where RF electrodes have to be integrated into the apertured plate, as known to the skilled man in the art, metal coatings and/or non-metal layers may be used for the production of the apertured plate, the electrodes and for the electrical wiring of such electrodes. As mentioned above, heat conductivity and capacity considerations may also be applied to material selection when required heat dissipation capabilities are required. According to another embodiment bulk or fractional electrodes may also be integrated into portions of the tip head in contact with the skin.

FIG. 11 shows another aspect of the present invention. A portion of apertured plate portion 124 has a having hole 118 as shown. According to this embodiment, scanned laser beam 119 hits plate 124 in an angle. Since the beam spot size is bigger than the diameter of hole 118 a portion of beam e.g., ray 131a will fall outside hole 118 and hit plate 124. However, a portion of the beam e.g. ray 131 may hit an internal surface of the hole 118 and be reflected into tissue 130 to ablate a tilted micro channel 133 by reflected ray 132. Laser scanner may be configured to rotate a tilted beam 119 around axis 120 of head 112 which will rotate a tilted beam 119 around axis A-A' of hole 118. Multiple tilted micro channels 133 may be created. Producing multiple micro channels having multiple surfaces while sharing a common surface is another way to maximize the ratio of surfaces over surfaces as mentioned above which is another aspect of the invention. As shown in FIG. 11, hole 118 may have a round geometry. In such a case, the rounded edges of hole 118 cause to at least part of beam 119 to be focused along at least one axis. Focusing the laser beam, which is characterized by a Gaussian energy distribution may increase the ablation efficiency. Internal reflection characteristics of the internal walls of the holes may be enhanced by a surface treatment or coating.

EXAMPLES

Figure 5:
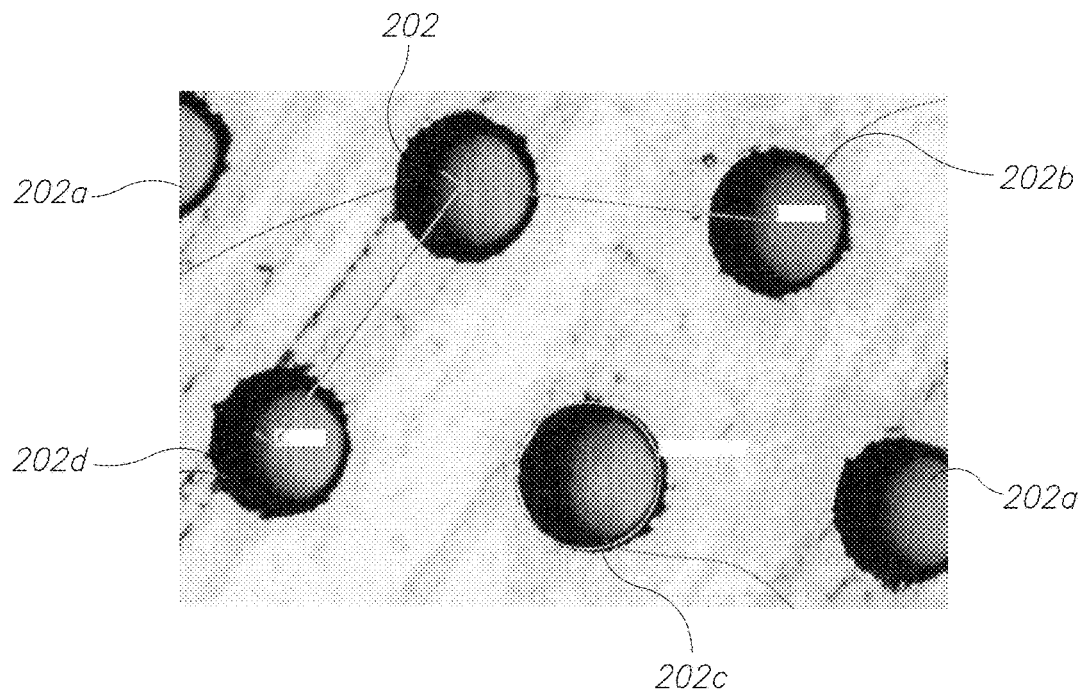
FIG. 5 illustrates an example of an apertured plate of the type described in FIGS. 6A-F.

Turning now to FIG. 5, this figure illustrates one embodiment of an apertured plate such as shown in FIGS. 4A to 4B. In FIG. 5, a plate 200 is shown as having apertures 202a-n. As shown, the apertures 202a-n are about 90 um in diameter and are spaced in a hexagonal format with center to center distances of about 200 um. These diameters and spacing are exemplary only and it is to be understood that different size apertures, different spacing between apertures and the pattern of the apertures are variable to suit the particular application, the particular treatment, the particular laser device and other factors. However, the FIG. 5 setup was used to test the efficacy of the aperture plate on test surfaces.

Figure 6:
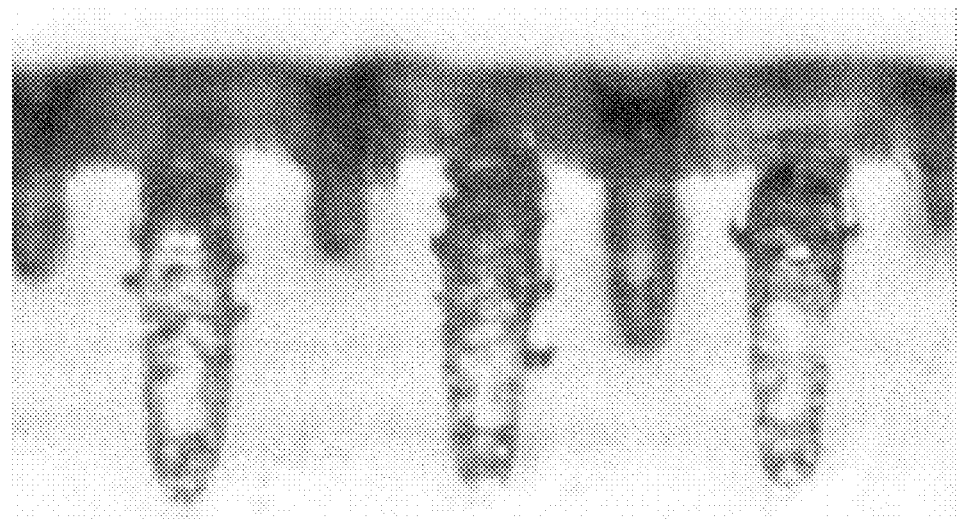
Figure 7A:
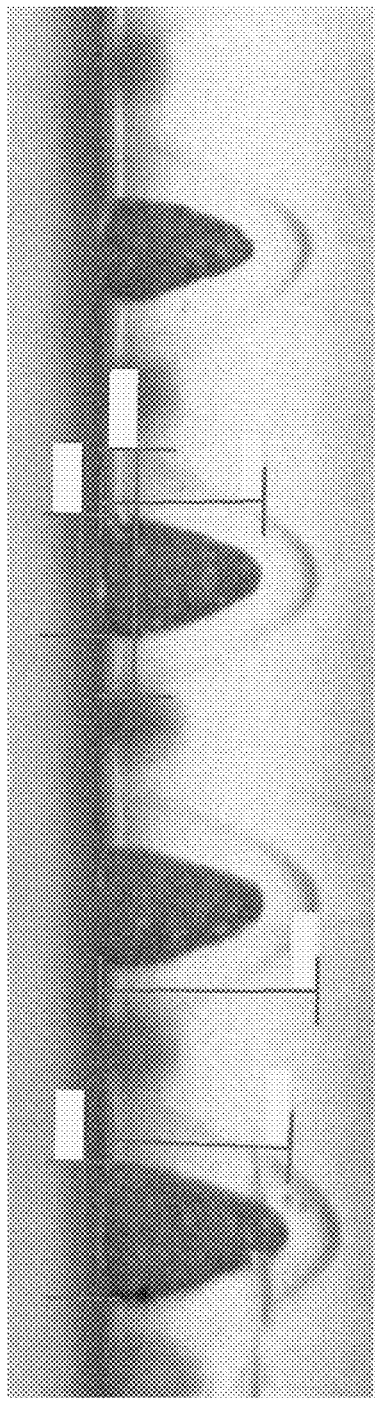
Figure 7B:
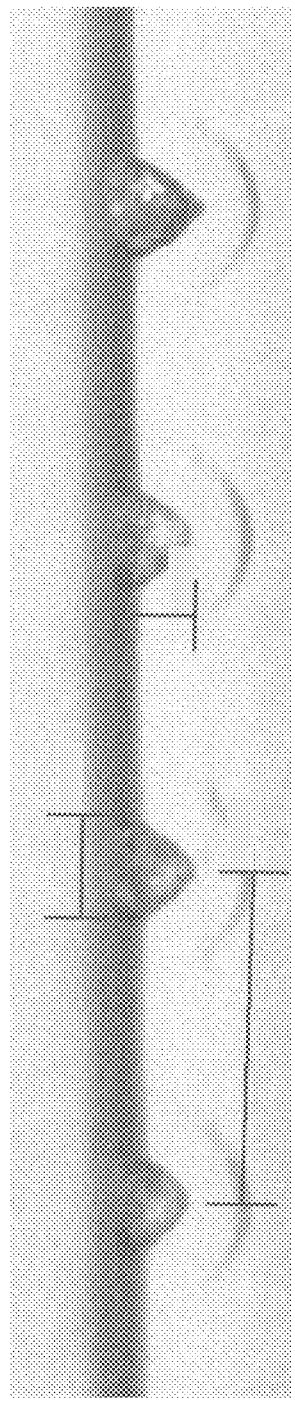
Figure 8A:
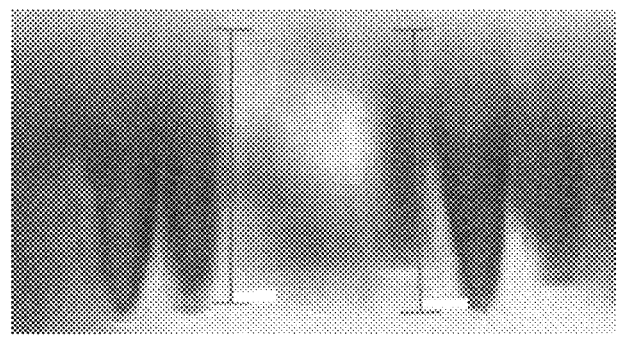
Figure 8B:
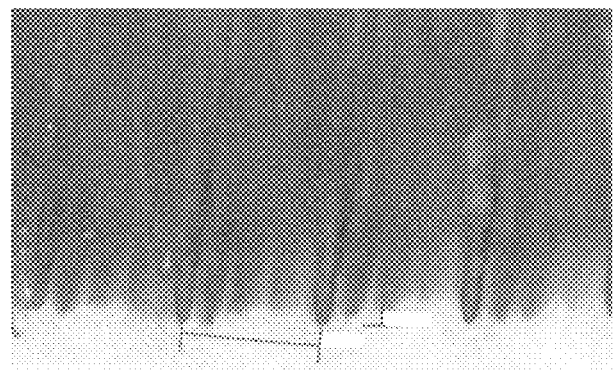
Figure 8C:
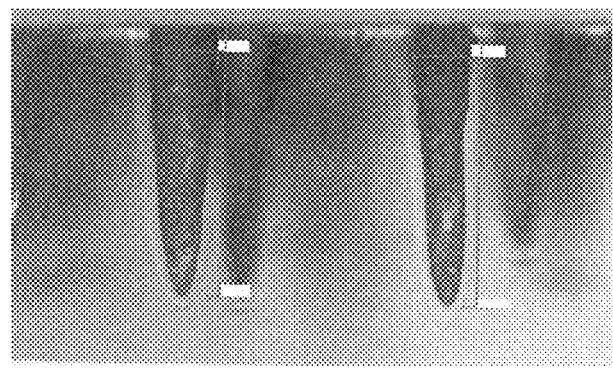

Again, looking at FIG. 5, it can be seen that the above-described apertured plate was connected through a head to the following devices, all of which are laser devices and scanners available from the assignee of the present invention, Lumenis Ltd. These devices include the Acupulse laser system used in conjunction with either the SurgiTouch scanner or the AcuScan 120 scanner, and UltraPulse laser device used with either SurgiTouch scanner or the DeepFX scanner. They are described on the Lumenis website. FIGS. 6, 7A and 7B and 8A to 8C illustrate the results of testing, first without the apertured plate and second with the use of the apertured plate. In FIG. 6, using a 40 W Acupulse set for a continuous scan mode, without the aperture plate the ablation depth is about 320 um. Using the 90 μm apertured plate of the present invention on the same Acupulse device and scan mode produces holes with diameters of about 55-60 um and channel or hole depths of about 250-280 um. As mentioned above, different interactions between holes' structure and property and the laser beam may dictate the characteristic of an ablated microchannel. In this non-limiting example, the diameter of the ablated microchannels is smaller than the diameter of the hole through which the microchannel has been produced. Therefore, it is another aspect of the present invention to use an array of holes characterized by a first diameter to produce a set of microchannels characterized by a second diameter wherein the first diameter is greater than the second diameter. In FIGS. 7A and 7B, using the AcuPulse laser scanner device, the results without the aperture plate, at 40 W, resulted in an ablated hole with diameters of about 95 um. Using the apertured plate having 90 um aperture diameter ablated micro channels of about 75 um in diameter and of about 95 um deep as seen in FIG. 7A. With the device set at 20 W, this resulted in holes that were about 60 um wide, 50 um deep holes that were very uniform as can be seen in FIG. 7B for this specific example. In FIG. 8A, an Ultrapulse laser device was used with a DeepFX scanner. In this setup, and with the device set up to produce 30 mJ, on a 90 um aperture diameter in an apertured plate an ablation depth of about 450 um was produced. Next, using 5 sequential pulses, without the apertured plate, the resulting holes were about 250 um in diameter and about 1.1 mm in depth as in FIG. 8B. With a 90 um-net in place the holes were about 150 um in diameter and about 0.6 mm in depth as in FIG. 8C.

FIG. 9 illustrates the theoretical minimal spot sizes, as limited by diffraction, for potential focal distances with the AcuPulse and the UltraPulse, based on the system M square and wavelength. As shown in FIG. 9, due to diffraction limit, the shorter the focal distance the smaller the spot size. In order to produce a microchannel having a diameter of 30 micron with an AcuPulse, or in order to produce a microchannel having a diameter of 21 microns with an UltraPulse the focal distance should be 10 mm. This means that t strong and expensive optics may be required to produce such a small spot size but would likely be too close to the tissue and may easily be contaminated by debris and therefore the optical efficiency will drop sharply. Thus, the embodiments shown in FIGS. 4A to 4B and as described herein in the accompanying text may be useful to implement.

What we claim is:
1. A method of producing small microchannels on a skin tissue surface while maintaining a 50 mm standoff distance from the skin tissue surface comprising:
    providing a lens system having:
    a plurality of aligned lenses;
    one or more scanning mirrors in line with and upstream of the plurality of aligned lenses and a source of laser energy upstream of the one or more scanning mirrors, wherein laser light beam from the laser source is transmitted from the source of laser energy, deflected by the one or more scanning mirrors and then transmitted through the aligned lenses;
    a first diverging beam lens of the plurality of aligned lenses downstream of the one or more scanning mirrors having negative refractive power;
    a second converging beam lens of the plurality of aligned lenses downstream of the first lens having positive refractive power;
    a third converging beam lens of the plurality of aligned lenses downstream of the second lens having positive refractive power; and,
    a fourth converging beam lens of the plurality of aligned lenses downstream of the third lens with positive refractive power;
    wherein the laser light beam exiting from the laser source is 7 mm in diameter, diverges to 12 mm after being transmitted through the first and the second lenses, enters the third lens with a 12 mm diameter, and converges to 70 microns on the focal plane after being transmitted through the third and fourth lenses;

the method comprising:

transmitting a laser light beam of 7 mm in diameter from the source of laser energy to impinge on the first lens;

transmitting the laser light beam through the first and second lenses, whereby the light beam diverges to 12 mm;

transmitting the diverged light beam to the third lens, the third lens collimating the light beam; and, transmitting the light beam from the third lens to the fourth lens, the fourth lens converging the light beam to produce 70 micron microchannel spots at a standoff distance of 50 mm from the vertex of the fourth lens at the skin tissue surface.

2. The method of claim 1, further comprising one or more motors to control the one or more scanning mirrors, a programmed controller in operative connection to the one or more motors, wherein the controller is programmed to move the one or more scanning mirrors in a selected pattern.

3. The method of claim 1, wherein the first lens is of meniscus shape with radii of curvature of 20.61 mm and 50.15 mm, the second lens is of meniscus shape with radii of curvature of 35.1 mm and 28.35 mm, the third and fourth lenses are identical and of meniscus shape with radii of curvature of 163.35 mm and 61.19 mm.

\* \* \* \* \*